United States Patent [19]

Anderson et al.

[11] Patent Number: 5,376,531
[45] Date of Patent: Dec. 27, 1994

[54] METHOD OF DETECTING CANCER

[75] Inventors: Byron E. Anderson, Morton Grove; Lyman E. Davis, Chicago, both of Ill.

[73] Assignee: Northwestern University, Evanston, Ill.

[21] Appl. No.: 939,830

[22] Filed: Sep. 3, 1992

[51] Int. Cl.[5] .................... G01N 33/574; G01N 33/53
[52] U.S. Cl. ..................... 435/7.23; 435/7.5; 435/7.9; 435/7.92; 435/7.94; 436/518; 436/64; 436/813
[58] Field of Search ............ 435/7.23, 7.92, 7.94, 435/7.9, 7.5; 436/518, 528, 64, 813

[56] References Cited

U.S. PATENT DOCUMENTS

| | | | |
|---|---|---|---|
| 4,137,401 | 1/1979 | Lemieux et al. | 536/116 |
| 4,174,385 | 11/1979 | Reid | 424/1 |
| 4,241,044 | 12/1980 | Kim | 424/1 |
| 4,563,445 | 1/1986 | Feizi et al. | 514/25 |
| 4,571,382 | 2/1986 | Adachi | 436/501 |
| 4,719,289 | 1/1988 | Kolar et al. | 530/331 |
| 4,725,557 | 2/1988 | Miyauchi et al. | 436/543 |
| 4,753,894 | 1/1988 | Frankel et al. | 435/240.27 |
| 4,783,420 | 11/1988 | DelVillano Jr. et al. | 436/518 |
| 4,946,830 | 8/1990 | Pulverer et al. | 514/23 |

FOREIGN PATENT DOCUMENTS

| | | |
|---|---|---|
| 44188 | 1/1982 | European Pat. Off. . |
| 106285 | 4/1984 | European Pat. Off. . |
| 63-17698 | 1/1988 | Japan . |

OTHER PUBLICATIONS

Kobata, et al., *Archives of Biochemistry and Biophysics*, 150, 273–281, 1972.

Anderson et al., "Tumor-associated blood group antigen expressions and immunoglobulins associated with tumors, " in *The Molecular Immunology of Complex Carbohydrates*, pp. 601–656 (Wu, ed. 1988).

Arends et al., "Distribution of monoclonal antibody-defined monosialoganglioside in normal and cancerous human tissues: An immunoperoxidsase study," *Hybridoma*, 2, 219 (1983).

Bray et al., "Incidence of elevated serum levels of CA-549 and CEA in breast cancer patients," *Clin. Chem.*, 34, 1296 (1988).

Bray et al., "Decreased levels of circulating lytic anti-T in the serum of patients with metastatic gastrointestinal cancer: a correlation with disease burden," *Clin. Exp. Immunol.*, 47, 176–182 (1982).

Collatz et al., "Further investigations of circulating antibodies in colon cancer patients: on the autoantigenicity of the carcinoembryonic antigen," *Int. J. Cancer*, 8, 298 (1971).

Davis et al., "Blood group (BG) antigen (Ag) expression by normal and squamous carcinoma epithelia," *Fed. Proc.*, 43, 1751 (1984).

Dohi et al., *Gastroenterol. Jpn*, 24, 238–245 (1989).

Dua et al., "Characterization of lacto-N-hexaose and two fucosylated derivatives from human milk by high-performance liquid chromatography and proton NMR spectroscopy," *J. Chrom.*, 17, 259–269 (1985).

Ernst, et al., "Monoclonal antibody localization of Lewis antigens in fixed tissue," *Lab. Invest.*, 50, 394–400 (1984).

Feller et al., "Mucin glycoproteins as tumor markers," in *Immunodiagnosis of Cancer*, pp. 631–672 (Herberman and Mercer, eds. 1990).

(List continued on next page.)

Primary Examiner—Toni R. Scheiner
Attorney, Agent, or Firm—Willian Brinks Hofer Gilson & Lione

[57] ABSTRACT

The invention provides a method of screening for gastrointestinal cancer in a mammal comprising: (a) contacting a body fluid taken from the mammal with N3; (b) measuring the amount of antibody to N3 in the body fluid; and (c) determining if the amount of antibody measured in step (b) is higher than the amount of antibody to N3 normally present in the same type of body fluid taken from mammals of the same species that do not have cancer. The invention also provides kits for screening for gastrointestinal cancer in a mammal by measuring the mammal's level of antibodies to N3.

20 Claims, 2 Drawing Sheets

Feller et al., in *Malignant Diseases*, pp. 167–294 (Baldwin, ed. 1987).

Frenoy et al., "Natural antibodies against the carcinoembryonic antigen (CEA) and a related antigen, NCA, in human sera," *Anticancer Research*, 7, 1229 (1987).

Galili et al., "Human natural anti-α-galactosyl IgG II. The specific recognition of α(1->3)-linked galocotose residues," *J. Exp. Med.*, 162, 573–82 (1985).

Gold et al., "Human anti-CEA antibodies detected by radioimmunoelectrophoresis," *Nature New Biology*, 239, 60–62 (Sep. 13, 1972).

Gold "Circulating antibodies against carcinoembryonic antigens of the human digestive system," *Cancer*, 20, 1663 (Oct. 1967).

Gooi, et al., "Marker of peripheral blood granulocytes and monocytes of man recognized by two monoclonal antibodies VEP8 and VEP9 involves the trisaccharide 3-fucosyl-N-acetyllactosamine," *Eur. J. Immunol.*, 13, 306–312 (1983).

Hakomori and Kannagi, "Carbohydrate Antigens in Higher Animals," in *Handbook of Experimental Immunology*, vol. 1, pp. 9.1–9.39, (Weir, ed. 1986).

Hakomori et al., "The hapten structure of a developmentally regulated glycolipid antigen (SSEA-1) isolated from human erythrocytes and adenocarcinoma: A preliminary note," *Biochem. Biophys. Res. Commun.*, 100, 1578–86 (1981).

Hakomori, "Aberrant glycosylation in tumors and tumor-associated carbohydrate antigens," *Adv. Cancer Res.*, 52, 257–331 (1989).

Hakomori and Kannagi, "Glycosphingolipids as tumor-associated and differentiation markers," *J. Nat. Cancer Inst.*, 71, 231–250 (1983).

Harmenberg et al., "Tumor markers carbohydrate antigens CA 19-9 and CA-50 and carcinoembryonic antigen in pancreatic cancer and benign diseases of the pancreatobiliary tract," *Cancer Res.*, 48, 1985 (1988).

Herlyn et al., "Increased sensitivity in detecting tumor-associated antigens in sera of patients with colorectal carcinoma," *J. Immunol. Methods*, 75, 15–21 (1984).

Howie et al., "Effect of neuraminidase on the expression of the 3-fucosyl-N-acetyllactosamine antigen in human tissues," *J. Clin. Pathol.*, 38, 409–416 (1985).

Huang et al., "Many monoclonal antibodies with an apparent specificity for certain lung cancers are directed against a sugar sequence found in lacto-N-fucopentaose III," *Arch. Biochem. Biophys.*, 220, 318–20 (1983).

Itzkowitz, et al., "Immunohistochemical comparison of Le$^a$, monosialosyl Le$^a$ (CA 19-9), and disialosyl Le$^a$ antigens in human colorectal and pancreatic tissues," *Cancer Res.*, 48, 3834–3842 (1988).

Itzkowitz et al., "Lewis$^x$-sialyated Lewis$^x$-related antigen expression in human malignant and nonmalignant colonic tissues," *Cancer Res.*, 46, 2627–2632 (1986).

Jozwiak and Koscielak, "Lactosylsphingosine-reactive antibody and CEA in patients with colorectal cancer," *Eur. J. Cancer Clin. Oncol.*, 18, 617–621 (1982).

Kannagi et al., "Quantitative and qualitative characterization of human cancer-associated serum glycoprotein antigens expressing fucosyl or sialyl-fucosyl type 2 chain polylactosamine," *Cancer Res.*, 46, 2619–2626 (1986).

Kjeldsen et al., "Preparation and characterization of monoclonal antibodies directed to the tumor-associated O-linked sialosyl-2->6 α-N-acetylgalactosaminyl (sialosyl-Tn) epitope," *Cancer Res.*, 48, 2214–20 (1988).

Klug et al., "Confirmation of a false-positive result in CA 125 immunoradiometric assay caused by human anti-idiotypic immunoglobulin,"*Clin. Chem.*, 34, 1071–1076 (1988).

Kobata and Ginsburg, "Oligosaccharides of human milk IV. Isolation and characterization of a new hexasaccharide, lacto-N-*neo*hexaose," *Arch. Biochem. Biophys.*, 150, 273–281 (1972).

Kobata, "Isolation of oligosaccharides from human milk," in *Complex Carbohydrates, Methods in Enzymology*, 28, pp. 262≧271 (Ginsburg, ed., Academic Press, New York, 1972).

Linsley et al., "Elevated levels of a high molecular weight antigen detected by antibody W1 in sera from breast cancer patients," *Cancer Res.*, 46, 5444–5450 (1986).

Lloyd et al., "Human monoclonal antibodies to glycolipids and other carbohydrate antigens: Dissection of the humoral immune response in cancer patients,"*Cancer Res.*, 49, 3445–3451 (1989).

Lo Gerfo et al., "Absence of circulating antibodies to carcinoembryonic antigen in patients with gastrointestinal malignancies," *Int. J. Cancer*, 9, 344 (1972).

U.S. PATENT DOCUMENTS

MacSween, "The antigenicity of carcinoembryonic antigen in man," *Int. J. Cancer*, 15, 246 (1975).

Magnani et al., "A monoclonal antibody-defined antigen associated with gastrointestinal cancer is a ganglioside containing sialylated lacto-N-fucopentaose II," *J. Biol. Chem.*, 257, 14365-69 (1982).

Magnani et al., "Identification of the gastrointestinal and pancreatic cancer-associated antigen detected by monoclonal antibody 19-9 in the sera of patients as a mucin," *Cancer Res.*, 43, 5489-92 (1983).

Magnani et al., "A monosialoganglioside is a monoclonal antibody-defined antigen of colon carcinoma," *Science*, 212, 55-56 (1981).

Pompecki et al., "Demonstration of elevated anti-Lewis antibodies in sera of cancer patients using a carcinoembryonic antigen-polyethylene glycol immunoassay," *Cancer Research*, 41, 1910-1915 (1981).

Rohr et al., *Soc. Complex Carbohydrates*, Oct. 1983.

Rohr et al., "Production of mouse monoclonal antibodies to blood group active oligosaccharides," *Fed. Proc.*, 42, 431 (1983).

Rohr et al., "Mouse monoclonal antibodies to blood group active oligosaccharides isolated from human breast milk," *Fed. Proc.*, 42, 2102 (1983).

Schuessler et al., "Blood group and blood-group-related antigens in normal pancreas and pancreas cancer: Enhanced expression of precursor type 1, Tn and sialyl-Tn in pancrease cancer," *Int. J. Cancer*, 47, 180-187 (1991).

Shi et al., "Expression of a carbohydrate differentiation antigen, stage-specific embryonic antigen 1, in human colonic adenocarcinoma," *Cancer Res.*, 44, 1142-1147 (1984).

Singhal et al., "Presence of fucolipid antigens with mono- and dimeric X determinant ($Le^x$) in the circulating immune complexes of patients with adenocarcinoma," *Cancer Res.*, 47, 5566-5571 (1987).

METHOD OF DETECTING CANCER

FIELD OF THE INVENTION

This invention relates to a method of detecting cancer comprising measuring a patient's level of antibodies to a particular tumor-associated antigen. The method is particularly useful for detecting cancer at an early stage of its development.

BACKGROUND OF THE INVENTION

Current assays for monitoring cancer generally measure the levels of tumor-associated antigens. Such assays frequently measure mucins and other glycoproteins or proteins apparently shed or secreted from the tumor into biological fluids such as serum. Tumors may also enhance the release of antigens from normal tissues into the blood stream so that levels rise during malignancy (e.g., CA 19-9 antigen). Common serological assays for tumor-associated antigens have been reviewed by Feller et al., in *Immunodiagnosis of Cancer*, pp 631–672 (Herberman and Mercer, eds. 1990) and in *Malignant Diseases*, pp. 167–294 (Baldwin, ed. 1987). Examples of such tests in general clinical use include those for carcinoembryonic antigen (CEA), CA 19-9, Ca 195, CA 125, B72.3 (TAG 72, Sialyl Tn), CA 50, CA 549, Du Pan-2 and CA 15-3 antigens. Less commonly; measured tumor-associated antigen markers include those for $Le^x$, dimeric $Le^x$, trimeric $Le^x$, CS $Le^x$, sialyl $Le^x$-i, disialyl $Le^a$, $Le^y$, i, T and Tn antigens. The vast majority of tumor-associated antigens presently measured exhibit alterations in carbohydrate expression and are classified as tumor-associated carbohydrate antigens (reviewed in Hakomori, *Adv. Cancer Res.* 52, 257–33 (1989)).

The currently employed measurements of tumor-associated antigens are of limited clinical utility because the levels of antigens they detect generally rise over the course of the disease and are most detectable in the later stages of cancer, but are infrequently elevated in the early stages of neoplastic disease. This association of tumor-associated antigen level with tumor burden and staging may account for the relatively poor ability such tests exhibit in the prediction of cancer or cancer reoccurrence, relegating the clinical application of such assays to a monitoring role. There are exceptional cases in which tumor antigen measurements are of high diagnostic value for early stage disease (Linsley et al., *Cancer Res.*, 46, 5444–5450 (1986)).

An alternative to measuring cancer antigen levels is to measure the immune response to tumor-associated antigens. For instance, Tal and associates (Tal et al., *Br. J. Cancer*, 18, 111–119 (1964)) have demonstrated that the sera from tumor patients and pregnant women contain antibodies that agglutinate tumor cells. Since lactose inhibited the agglutination, it was suggested that the antibodies were directed to lactosylceramide. Subsequently, elevated levels of antibody directed to lactosyl sphingosine were detected in a number of patients with gastrointestinal cancer (Jozwiak and Koscielak, *Eur. J. Cancer Clin. Oncol.*, 18, 617–621 (1982)).

The specificity of human monoclonal antibodies derived from cancer patients has also been examined (reviewed in Lloyd, et. al., *Cancer Res.*, 49, 3445–3451 (1989)). These human monoclonal antibodies were found to exhibit specificities to gangliosides (GM3, GM2, GD3, GD2), Forssman antigen, galactosylgloboside, lacto-N-tetraose, and i antigen.

The presence of antibody to tumor-associated antigens in cancer patients has been investigated for a number of other tumor markers. These tumor markers include CEA, $Le^x$, T and Tn antigens.

CEA is a glycoprotein containing multiple antigenic epitopes on both the oligosaccharide and peptide portions of the molecule. It is an embryonic antigen not normally present on adult tissues, but it is found in all human digestive system cancers. Thus, the presence of CEA on tissue, or the presence of circulating CEA, may be indicative of digestive system cancer. Whether antibodies to CEA are found in normals or cancer hosts has been controversial. See, Staab et al., *Br. J. Cancer*, 42, 26 (1980); Frenoy et al., *Anticancer Research*, 7, 1229 (1987). It has been reported that anti-CEA antibodies are found in patients with non-metastatic digestive system cancer and in pregnant and postpartum women, but not in normals or those with metastatic cancer. Gold, *Cancer*, 20, 1663 (October 1967). These results have been refuted by others. See Lo Gerfo et al., *Int. J. Cancer*, 9, 344 (1972); Collatz et al., *Int. J. Cancer*, 8, 298 (1971).

MacSween has reported the detection of antibodies to CEA, but suggests that the binding to CEA represents the cross-reactivity of antibodies to similar antigens, such as blood group antigens. MacSween, *Int. J. Cancer*, 15, 246 (1975). In fact, elevated levels of anti-CEA antibodies directed to $Lewis^{ab}$ substances on a CEA preparation have been found in women, smokers and 7–23% of patients having colonic, breast and bronchogenic carcinoma. Pompecki et al., *Cancer Research*, 41, 1910–1915 (1981). Pompecki et al. suggest that an increase in the levels of these antibodies is a poor prognostic sign for cancer patients and that following the levels of antibodies to blood group determinants, and perhaps other carbohydrate determinants, may be useful in monitoring disease progress in certain types of cancer and other diseases. Id.

Another group has reported circulating anti-CEA IgG antibodies in a very small number (3/500,000) of sera obtained from cancer patients. Ura et al. *Cancer Letters*, 25, 283 (1985). More recently, anti-CEA antibodies of weak affinity directed to the peptide portion of CEA were found in all normal and pathological sera tested using an enzyme immunoassay. Frenoy et al., *Anticancer Research*, 7, 1229 (1987). Finally, circulating CEA immune complexes have been described. Staab et al., *Br. J. Cancer*, 42, 26 (1980). Staab et al. teach that the presence of CEA immune complexes is a poor prognostic indicator for cancer patients. Id.

T and Tn are also tumor-associated antigens. While T and Tn are present on most tissues, they are normally occluded by covering structures which make them inaccessible to the immune system. T and Tn in unmasked immunoreactive form have been reported to be abundantly expressed in about 90% of carcinoma tissues. Springer, *Science*, 224, 1198–1206 (1984). The relative proportion and density of T and Tn on tumor surfaces have also been reported to correlate with tumor aggressiveness and invasiveness. Id. In particular, Tn is believed to be an important antigen in carcinoma metastasis. Id. All humans are reported to have antibodies against T and Tn which are thought to be elicited predominantly in response to antigens of the intestinal flora. Springer, *Science*, 224, 1198–1206 (1984). There have been reports that levels of anti-T are depressed, elevated or unchanged in cancer patients. See Bray et al., *Clin. Exp. Immunol.*, 47, 176–182 (1982).

For instance, U.S. Pat. No. 4,241,044 (Kim) teaches that carcinoma patients generally have elevated levels of anti-T. However, Bray et al. teach that patients with metastatic gastrointestinal cancer have depressed serum levels of anti-T and that the levels of anti-T correlate with the level of disease in that 83% of patients with extensive disease had lower than normal levels of anti-T as compared to 45% of patients with moderate disease and none with minimal disease. Bray et al., *Clin. Exp. Immunol.*, 47, 176–182 (1982).

It has also been reported that patients with carcinoma generally have depressed levels of anti-T as compared to normals or to patients with benign diseases, but that in rare instances patients with carcinoma have elevated levels of anti-T. Springer, *Science*, 224, 1198–1206 (1984); Springer et al. in *Cellular Oncology: New approaches in Biology, Diagnosis and Treatment*, pages 99–130 (Moloy and Nicolson eds., 1982).

Finally, Thatcher et al. teach that anti-T titers are subnormal in patients with disseminated melanoma before therapy, and that patients who responded to therapy had significantly higher titers than did nonresponders in sera taken before therapy, at regression or progression of disease, and during the last pulse of treatment. Thatcher et al., *Cancer*, 46, 1378 (1980). Higher pretreatment titers were also associated with a significantly longer survival time. Id.

N3 is reported to be a mixture of difucosyl lacto-N-hexaoses and difucosyl lacto-N-neohexaoses which is isolated from breast milk. Kobata and Ginsburg, *Arch. Biochem. Biophys.*, 150, 273–281 (1972). Lacto-N-hexaose has the formula: Galβ1→4GlcNAcβ1→6-(Galβ1→3GlcNAcβ1→3)Galβ1→4Glc. Id. Lacto-N-neohexaose had the formula: Galβ1→4GlcNAcβ1→6-(Galβ1→4GlcNAcβ1→3)Galβ1→4Glc. Id. Kobata and Ginsburg speculate that the two fucose residues may be attached α1→2 to galactose, α1→3 to N-acetylglucosamine, α1→4 to N-acetylglucosamine, or α1→3 to glucose. Id. The exact composition of N3 will vary depending on the Lewis blood type of the donor. Id.

N3 isolated from the breast milk of individuals of Lewis blood type Le(a+b−) contains an octasaccharide having the following formula I:

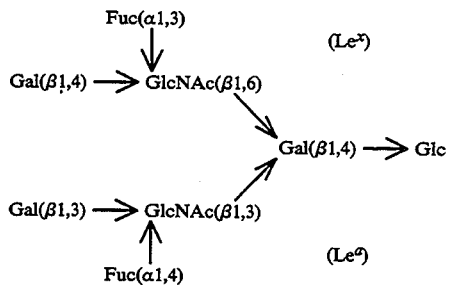

Dua et al., *J. Chrom.*, 17, 259–269 (1985). This octasaccharide is the predominant isomer, comprising at least 90% of the N3 isolated from Lewis (a+b−) individuals. Id. Dua et al. were unable to demonstrate the presence of difucosyl lacto-N-neohexaoses in their N3 preparation. Id. Based on the limits of their methodology they, therefore, concluded that N3 isolated from Lewis (a+b−) individuals contained at most 10% of such difucosyl lacto-N-neohexaoses. Id. Note that N3 is referred to as M3 in the Dua et al. article.

The immunodeterminant structure of the $Le^a$ blood group antigen is the trisaccharide Galβ1→3-(Fucα1→4)GlcNAc, which is carried by a type 1 blood group chain. The immunodeterminant structure of $Le^x$ is the trisaccharide Galβ1→4(Fucα1→3)GlcNAc which is carried by a type 2 blood group chain. $Le^x$ is also sometimes designated 3-fucosyl-N-acetyl-lactosamine, X hapten, Cluster of Differentiation (CD) 15 leukocyte antigen in humans, and stage-specific embryonic antigen 1 (SSEA-1) in mice. As can be seen from an examination of the above formula I, N3 isolated from Lewis (a+b−) individuals contains $Le^a$ and $Le^x$ determinants. Accordingly, as would be expected, N3 isolated from Lewis (a+b−) individuals displays $Le^a$ and $Le^x$ hapten activity in hemagglutination assays. Id.; Rohr et al., *Fed. Proc.*, 42, 2102 (1983); Rohr et al., *Fed. Proc.*, 42, 431 (1983); Rohr et al., *Soc. Complex Carbohydrates*, October 1983.

In epithelial-derived cancers of the colon and pancreas, the $Le^a$ blood group antigen is not considered a tumor-associated antigen because of its prominent expression in both normal and cancer tissues. Itzkowitz, et al., *Cancer Res.*, 48, 3834–3842 (1988); Yuan, et al., *Cancer Res.*, 45, 4499–4511 (1985); Ernst, et al., *Lab. Invest.*, 50, 394–400 (1984). $Le^x$ is present on a variety of normal cells such as kidney tubules, gastrointestinal epithelia and granulocytes, and it accumulates in a variety of human cancers including those of leukocyte, stomach, liver, lung, and colon origin. Gooi, et al., *Eur. J. Immunol.*, 13, 306–312 (1983); Hakomori, *Adv. Cancer Res.*, 52, 257–331 (1989); Hakomori, *J. Nat. Cancer Inst.*, 71, 231–250 (1983).

For instance, $Le^x$ antigen accumulates in gastrointestinal cancers in both membrane-bound forms (glycolipids and glycoproteins) and secreted forms (glycoproteins and mucins). The membrane-bound forms are generally detected by immunocytochemical means, while the secreted forms are assayed using standard immunoassay methods.

The expression of $Le^x$ antigen on tissue occurs at a higher frequency in early gastric cancer (93.3%) than in advanced stage cancer (66.7%), and $Le^x$ is present in 81% of cases of histologically classified undifferentiated gastric cancer and 66.7% of differentiated gastric cancer. Dohi et al., *Gastroenterol. Jpm*, 24, 239–245 (1989). Increased levels of the expression of $Le^x$ antigen on tissues have also been observed in pancreatic cancer and colorectal adenocarcinomas. Schuessler et al., *Int. J. Cancer*, 47, 180–187 (1991); Shi et al., *Cancer Res.*, 44, 1142–1147 (1984); Itzkowitz et al., *Cancer Res.*, 46, 2627–2632 (1986).

Immunoassays measuring levels of $Le^x$ in the sera of cancer patients have given mixed results. Kannagi et al., *Cancer Res.*, 46, 2619–2626 (1986) report that levels of $Le^x$ and $polyLe^x$, while occasionally high, were elevated in only about 10% of the cancer sera tested. These authors also reported that serum levels of sialyl $Le^{x}$-i were significantly high in patients with cancers originating from organs from which adenocarcinomas often develop, and that the serum levels of $Le^y$ were frequently high in patients with hepatoma. They concluded that all four antigens ($Le^x$, $polyLe^x$, sialyl $Le^{x}$-i and $Le^y$) were tumor-associated antigens.

Herlyn et al., *J. Immunol. Methods*, 75, 15–21 (1984) reports that 53% of colorectal cancer patients older than 65 years had elevated levels of antibodies to lacto-N-fucopentaose (LNF) III compared to none of age-matched, apparently healthy donors or patients with benign gastrointestinal tract lesions and 18% of patients with inflammatory gastrointestinal tract diseases. In younger patients, the differences were less marked, and LNF III is found at relatively high levels in normals under 25 years of age. LNF III is a carbohydrate containing a $Le^x$ determinant.

A good correlation between $Le^x$ levels and the stage of colon cancer has been reported when two high affinity monoclonal antibodies directed to mono-$Le^x$ and dimeric-$Le^x$ structures were used for the assay of $Le^x$ levels in colorectal adenocarcinoma sera. Singhal et al., *Cancer Res.*, 50, 1375-1380 (1990). Singhal et al. report that the preoperative levels of serum $Le^x$ increased in association with the progression of colorectal cancer (Dukes stages A to D) after surgery. In particular, they found that the percentage of serum $Le^x$ above the upper normal control level of 10 ng/ml were as follows:

| | |
|---|---|
| Dukes A | 20% |
| Dukes B, with recurrent cancer | 41% |
| Dukes B, without recurrent cancer | 46% |
| Dukes C, with recurrent cancer | 68% |
| Dukes C, without recurrent cancer | 67% |
| Dukes D | 74%. |

A longitudinal study of Dukes B and C patients having $Le^x$ levels of greater than 20 ng/ml was performed by these researchers. In Dukes C patients exhibiting cancer recurrence, postoperative $Le^x$ levels rose significantly twenty-four months after surgery, while Dukes C patients without cancer recurrence showed a decrease in $Le^x$ antigen levels over the same period. In Dukes B patients, postoperative levels of $Le^x$ did not rise in patients with or without recurrence of cancer over the same twenty-four month period. The $Le^x$ antigen detected by these researchers was expressed on a large molecular weight glycoprotein ($M_r$ about 200,000). This glycoprotein is apparently different from the glycoproteins bearing the CEA or sialyl-$Le^a$ (19-9) antigens. The $Le^x$ glycoprotein was shown to be present in 85% of the sera of adenocarcinoma patients and in 33% of normal sera. The authors suggest that serum $Le^x$ antigen levels could be of diagnostic and prognostic value in adenocarcinoma.

The existence of human antibodies to $Le^x$ has been demonstrated by the isolation of circulating immune complexes (CIC) from the sera of adenocarcinoma patients which, upon dissociation, were shown to contain antibodies reactive with purified glycolipids bearing $Le^x$ antigen and an antigen component expressing $Le^x$ antigen(s). Singhal et al., *Cancer Res.*, 47, 5566-5571 (1987). These investigators found that significantly higher levels of these CICs could be detected in patients suffering from breast, lung and colon adenocarcinoma as compared to controls (normals and melanoma patients) and that these CICs were detected in much higher percentages of adenocarcinoma patients than was the sialyl-$Le^x$ antigen.

Thus, while N3 itself has not been demonstrated to be a tumor-associated antigen, the $Le^x$ determinant, which is part of the N3 oligosaccharide, is a tumor-associated structure preferentially expressed on tumors. See, e.g., Davis et al., *Fed. Proc.*, 43, 1751 (1984); Anderson et al., in *The Molecular Immunology of Complex Carbohydrates*, pp. 601-656 (Wu, ed. 1988); Hakomori and Kannagi, "Carbohydrate Antigens in Higher Animals," in *Handbook of Experimental Immunology*, Volume 1, pp. 9.1-9.39, (Weir, ed. 1986); Pompecki et al., *Cancer Research*, 41, 1910-1915 (1981). Also, significantly higher levels of CICs containing antibodies to $Le^x$ could be detected in adenocarcinoma patients as compared to controls. However, Applicants are not aware of any reports of the presence or changed levels of uncomplexed antibodies to $Le^x$ in cancer patients.

SUMMARY OF THE INVENTION

The invention comprises a method of detecting cancer in a mammal by measuring the amount of antibody to N3 present in a body fluid taken from the mammal. The method comprises: (a) contacting the body fluid taken from the mammal with N3; (b) measuring the amount of antibody to N3 in the body fluid; and (c) determining if the amount of antibody measured in step (b) is higher than the amount of antibody to N3 normally present in the same type of body fluid taken from mammals of the same species that do not have cancer. N3 is described in the Background section above and is further described below.

The invention also comprises a kit for detecting cancer in a mammal by measuring the levels of antibodies to N3 in a body fluid of the mammal. In one embodiment, the kit comprises a container of labeled N3. In another embodiment, the kit comprises a container of N3 which has been conjugated to a protein or polypeptide, and these N3-conjugates may be labeled or unlabeled. In a third embodiment, the kit comprises a container of N3 and a container of a secondary antibody or another reagent which binds to the anti-N3 antibodies. The secondary antibody or other reagent may be labeled or unlabeled.

The method and kit of the invention are particularly useful for detecting cancer at an early stage of its development.

DETAILED DESCRIPTION OF THE PRESENTLY PREFERRED EMBODIMENTS

Figure 1:
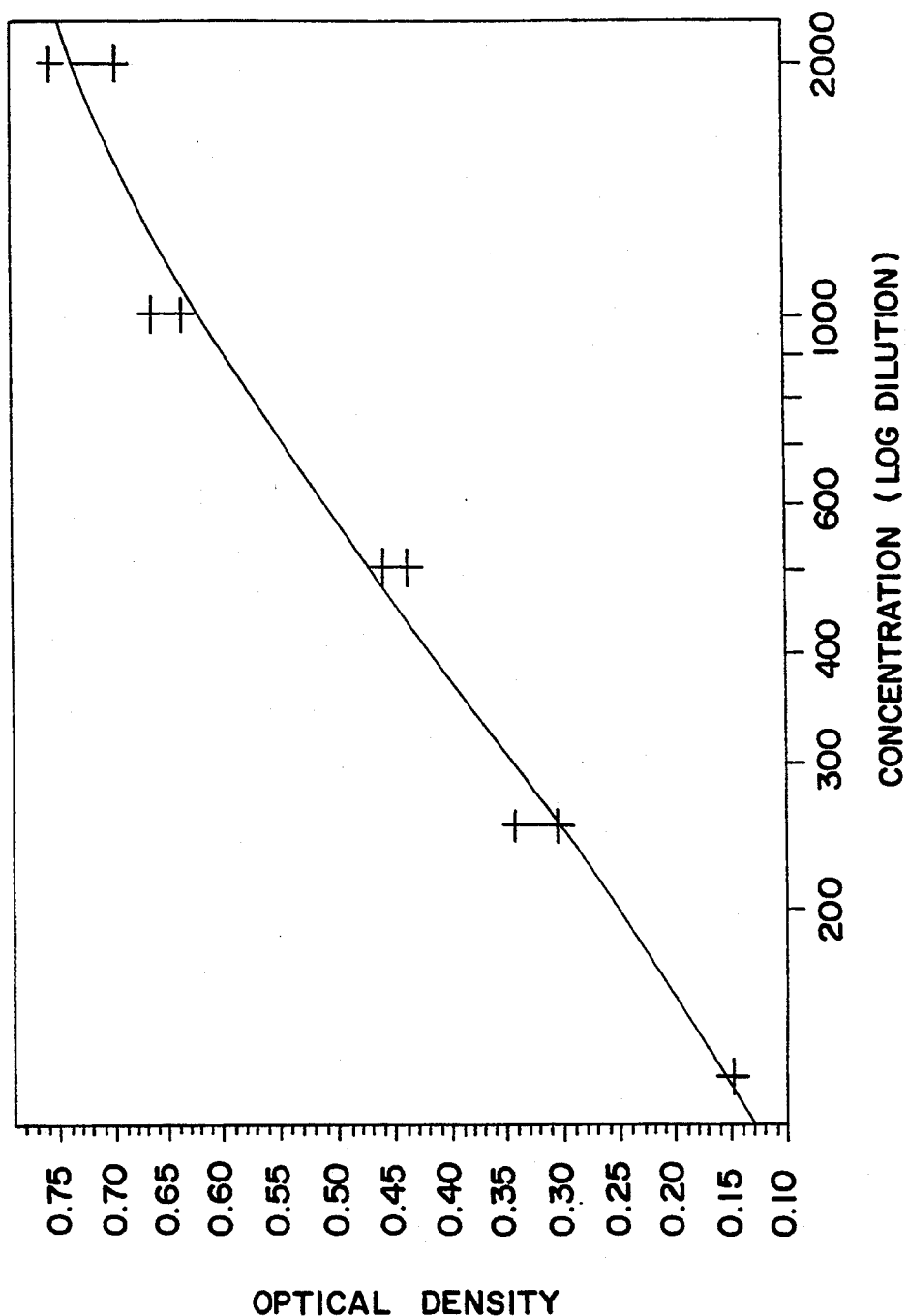
FIG. 1: Representative graph of output of the Titercalc program which was used to perform non-linear regression on data obtained by titrating antibodies to N3 in sera from normals and from patients suffering from gastrointestinal cancer.

The method used to measure the amount of antibody to N3 in a mammalian body fluid may be any immunoassay technique that allows for quantitation of antibody. Suitable techniques include fluorescence immunoassay, radioimmunoassay, chemiluminescent immunoassay, and enzyme immunoassay. The immunoassay employed may be a homogeneous or heterogeneous assay, may be a competitive or an immunometric assay, or may be a direct binding or inhibition assay. Such immunoassay techniques are well known and conventional.

Since the antibodies to N3 may be low titer or low affinity antibodies, preferred immunoassays are those employing N3 conjugated to a carrier protein or polypeptide (N3-conjugate), the N3-conjugate being immobilized on a solid surface. Also preferred for the same reasons are immunoassays that employ an amplified signal. Examples of preferred assays include solid phase heterogeneous assays having N3-conjugate immobilized on a solid surface, enzyme immunoassays that employ an amplified signal, and enzyme-linked immunosorbent assays (ELISA) which employ both a solid surface and an amplified signal. Particularly preferred is the direct binding enzyme-linked fluorescence assay (ELFA) described in Example 1 below.

The specific concentrations, the temperature and time of incubation, as well as other assay conditions for whatever immunoassay is chosen, can be varied depending on such factors as the nature of the sample, the concentration of antibody in the sample, and the like. Those skilled in the art will be able to determine operative and optimal assay conditions for each determination while employing routine experimentation.

Any body fluid containing antibodies to N3 can be used in the method of invention, including serum, plasma, saliva and urine. Serum or plasma is preferred.

N3 suitable for use in the invention may be prepared as described in Kobata, in *Complex Carbohydrates, Methods in Enzymology*, 28, pp. 262-271 (Ginsburg, ed., Academic Press, New York, 1972); Kobata and Ginsberg, *Arch. Biochem. Biophys.*, 150, 273-281 (1972); Dua et al., *J. Chrom.*, 17, 259-269 (1985). N3 is also available commercially from Accurate Chemical and Scientific Corp., Westbury, N.Y.

N3 may be used as such in the method of the invention or, as noted above, may be conjugated to a carrier protein or polypeptide (N3-conjugate). Suitable carrier proteins and polypeptides are well-known. They include but are not limited to: albumins, such as bovine serum albumin (BSA), ovalbumin and human serum albumin; hemocyanins such as keyhole limpet hemocyanin (KLH); bovine thyroglobulin; gelatin such as bovine, porcine and cold fish skin; gamma globulins such as bovine, chicken, and human; and various synthetic polypeptides such as poly-L-lysine, poly-DL-alanine-poly-L-lysine. Methods for conjugating N3 to these proteins and polypeptides are conventional and well-known. Preferred methods include reductive amination, conjugation using phenylisothiocyanate derivatives, p-aminophenyl derivatives, hydrazide derivatives, thiosemicarbazide derivatives, diazo coupling using phenethylamine derivatives and conjugation following appropriate modification using glutaraldehyde, carbodiimides (such as 1-(3-dimethylaminopropyl)-3-ethylcarbodiimide hydrochloride (ECDI)), N-N-carbonyldiimidazole, 1-hydroxybenzotriazole monohydrate, N-hydroxysuccinimide, N-trifluoroacetylimidazole or cyanogen bromide.

Suitable solid surfaces for use in solid phase assays include polystyrene, polyacrylamide, polymethylmethacrylate, polycarbonate, polysulfone, polyacrylonitrile, polyethylene, polypropylene, dextran, glass, nylon, polyvinyl alcohol, gels, clay and cellulose derivatives, as well as other polymeric materials. N3, N3-conjugate, secondary antibody or other reagent reactive with anti-N3 antibodies may be immobilized on the solid surface for a solid phase assay. These materials may be immobilized noncovalently or covalently on the solid surface, and their attachment may be enhanced by the use of conventional linking agents which are part of, or derivatized onto, polymeric solid surfaces. These linking agents include diimidoesters, carbodiimide, periodate, alkylhalides, dimethylpimelimidate and dimaleimides. See Blair and Ghose, *J. Immunol. Methods*, 49, 129 (1983); Blair and Ghose, *Cancer Res.*, 41, 2700 (1981); Gautheir, *J. Exp. Med.*, 156, 766 (1982); Wong, S. S. in *Chemistry of Protein Conjugation and Cross-linking*, pp. 1-324 (CRC Press 1991).

To quantitate the antibody to N3 in the body fluid, labeled N3 or N3-conjugate may be used. When an N3-conjugate is used, the label may be on the N3 or on the protein or polypeptide.

Alternatively, the antibodies to N3 in a body fluid may be quantified using a labeled secondary antibody, or fragment thereof, that binds selectively to the anti-N3 antibodies of the mammal from which the body fluid is taken. The secondary antibody may be an antiserum, a purified fraction of such antisera (such as DE-52 fractions or affinity-purified antibody), a monoclonal antibody, or fragments of antibodies that are capable of binding antigen (such as Fab, F(ab')$_2$, and Fab' fragments). Methods of making antibodies and of purifying, fractionating, fragmenting and labeling them are conventional and well-known. Harlow, E. and Lane, D. in *Antibodies: A Laboratory Manual*, pp 1-726 (Cold Spring Harbor Laboratory 1988). Also, many suitable secondary antibodies are available commercially.

Instead of a labeled secondary antibody, any other labeled reagent which binds to the anti-N3 antibodies may be used. Such reagents include bacterial immunoglobulin binding proteins such as Protein A and Protein G. See Boyle, in *Bacterial Immunoglobulin Binding Proteins, Vol. 2: Applications in Immunotechnology*, pp 1-475 (Academic Press 1990).

Labels useful in the invention and methods of attaching them to antigens, antibodies and other immunoassay reagents such as Protein A or Protein G are known in the art. Suitable labels include radioactive isotopes, enzymes, chemiluminescent labels, bioluminescent labels and fluorescent labels.

Enzyme-labeled antigens, antibodies and other reagents, when later exposed to the enzyme's substrate, will react with the substrate in such a manner as to produce a chemical moiety which can be detected by, for example, spectrophotometric, fluorometric, chemiluminescent, or potentiometric means. Examples of enzymes that can be used as detectable labels are horseradish peroxidase, lactoperoxidase, lactate dehydrogenase, lysozyme, luciferase, penicillinase, phospholipase C, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, $\alpha$ amylase, $\beta$ amylase, glucoamylase, hexokinase, beta-galactosidase, $\beta$ glucosidase, ribonuclease, urease, catalase, glucose-6-phosphate dehydrogenase, glucoamylase, pyruvate kinase, carbonic anhydrase and acetylcholine esterase.

Alternatively, the antigen, antibody or other reagent can be labeled with a radioactive isotope. The presence of the radioactive isotope would then be determined by such means as the use of gamma counter or a scintillation counter. Isotopes which are particularly useful are $^3$H, $^{125}$I, $^{32}$P, $^{35}$S, $^{14}$C, $^{51}$Cr, $^{36}$Cl, $^{57}$Co, $^{58}$Co, $^{59}$Fe, $^{75}$Se, $^{111}$In, $^{99m}$Tc, $^{67}$Ga, and $^{90}$Y.

Antigens, antibodies and other reagents with a fluorescent label may also be used. When the fluorescently-labeled molecule is exposed to light of the proper wavelength, its presence can then be detected because of the resulting fluorescence. Among the most important fluorescent labeling compounds are fluorescein isothiocyanate, rhodamine, phycoerythrin, phycocyanin, allophycocyanin, o-phthaldehyde, fluroescamine, 7-amino-4-methylcoumarin-3 acetic acid, 7-amino-4-methylcoumarin-3 acetyl hydrazide, and succinimidyl 7-amino-4-methylcoumarin-3-acetate.

Fluorescence emitting metal atoms such as Eu (europium), and other lanthanides, can also be used. These can be attached to the desired molecule by means of metal-chelating groups, such as DTPA or EDTA.

Another way in which the antibody, antigen or other reagent can be detectably labeled is by coupling it to a chemiluminescent compound. The presence of the chemiluminescent-tagged molecule is then determined by detecting the presence of luminescence that arises during the course of a chemical reaction. Examples of particularly useful chemiluminescent labeling compounds are luminol, isoluminol, aromatic acridinium ester, imidazole, acridinium salt, peroxidase (for enhanced chemiluminescence) and oxalate esters.

Likewise, a bioluminescent compound may be used as a label. Bioluminescence is a special type of chemiluminescence which is found in biological systems and in which a catalytic protein increases the efficiency of the chemiluminescent reaction. The presence of a bioluminescent molecule would be determined by detecting the presence of luminescence. Important bioluminescent compounds for the purpose of labeling are luciferin, luciferase, and aequorin.

To quantitate the antibodies to N3, the antigen (i.e., N3 or N3-conjugate), secondary antibody or other reagent reactive with N3 antibodies may be biotinylated. The biotinylated antigen, antibody or reagent is then reacted with avidin or streptavidin labeled with any of the labels listed above. Especially preferred are avidin and streptavidin labeled with enzymes. Methods of making and using biotinylated reagents are well-known.

In a similar manner, the antigen, secondary antibody or other reagent can be labeled with a hapten (such as dinitrophenol or digoxin). The hapten-labeled molecule is then reacted with an antibody to the hapten, this anti-hapten antibody being labeled with any of the labels listed above. This so-called "hapten sandwich" procedure is well-known in the art.

A labeled secondary antibody or other labeled reagent reactive with the anti-N3 antibodies may be used to quantitate the anti-N3 antibodies in a body fluid using the known immunoassay techniques described above. For instance, N3-conjugate may be immobilized on a solid surface such as the wells of a microtiter plate. After washing off unbound N3-conjugate, the N3-conjugate immobilized on the solid surface is contacted with a body fluid sample, such as a sample of human serum, and antibody to N3 in the sample will bind to the immobilized N3-conjugate. Unbound materials are washed away, and a labeled secondary antibody, such as enzyme-labeled antibody to human immunoglobulin, is added. The labeled secondary antibody binds to the anti-N3 antibodies and can be used to quantitate the anti-N3 antibodies after the unbound labeled component is washed away. For example, adding the substrate for the enzyme present on enzyme-labeled secondary antibody to human immunoglobulin causes a measurable change in a property, often an increase in fluorescence, and the change in the property can be used to quantitate the anti-N3 antibodies. Another labeled reagent reactive with the anti-N3 antibodies (such as labeled Protein A or Protein G) may be used instead of the labeled secondary antibody.

Alternatively, an unlabeled secondary antibody or another unlabeled reagent reactive with the anti-N3 antibodies may be immobilized on a solid surface and then contacted with a body fluid sample. Antibodies to N3 in the sample (along with other antibodies) will bind to the immobilized secondary antibody or other reagent. After unbound materials are washed away, labeled N3 or N3-conjugate is added. The labeled N3 or N3-conjugate binds to the anti-N3 antibodies and can be used to quantitate the anti-N3 antibodies. Suitable secondary antibodies and other reagents reactive with N3 antibodies useful in such an assay include those described above, but in unlabeled form.

The final step of the method of the invention requires that it be determined whether the amount of antibody to N3 measured in a body fluid of a mammal possibly having cancer is higher than the amount of antibody to N3 normally present in the same type of body fluid taken from mammals of the same species that do not have cancer. This step can be accomplished using well-known and conventional statistical methods and is most conveniently accomplished using a computer.

A test kit for quantitating antibodies to N3 is also part of the invention. In one embodiment, the kit comprises a container of labeled N3. In another embodiment, the kit comprises a container of N3-conjugate. The N3-conjugate may be labeled or unlabeled. In a third embodiment, the kit comprises a container of N3 and a container of a secondary antibody or other reagent which reacts with anti-N3 antibodies. In this third embodiment, the N3 may be labeled, unlabeled, or conjugated to a protein or polypeptide, and the secondary antibody or other reagent may be labeled or unlabeled.

Suitable containers include bottles, vials, tubes, and microtiter plates.

The N3 or N3-conjugate may be in solution, may be lyophilized or may be immobilized on a solid surface. The solid surfaces are of the types described above, and the N3 or N3-conjugate is immobilized as described above. Thus, the container may be a bottle holding a solution of N3, a vial of lyophilized N3, or may be a microtiter plate, the wells of which are coated with N3-conjugate.

The secondary antibody or other reagent may be in solution, may be lyophilized or may be immobilized on a solid surface. The solid surfaces are of the types described above, and the secondary antibody or other reagent is immobilized as described above. Thus, the container may be a bottle holding a solution of secondary antibody or other reagent, a vial of lyophilized secondary antibody or other reagent, or may be a microtiter plate, the wells of which are coated with secondary antibody or other reagent.

As noted above, the N3, N3-conjugate, secondary antibody or other reagent reactive with N3 antibodies may be labeled if it is to be used for quantitating the anti-N3 antibodies in the body fluid. Suitable labels are those listed above.

In addition, the kit may contain other materials which are known in the art and which may be desirable from a commercial and user standpoint such as buffers, diluents, standards, control sera, etc. The kit may also include empty containers useful for performing the immunoassay.

EXAMPLES

EXAMPLE 1: Assay for Antibodies to N3 in the Sera of Gastrointestinal Cancer Patients A. Preparation of Screening Antigen N3 was isolated from human milk from an individual of Lewis blood type Le(a+b−) by gel filtration and paper chromatography as described in Kobata, in *Complex Carbohydrates, Methods in Enzymology*, 28, pp. 262–271 (Ginsburg, ed., Academic Press, New York, 1972); Kobata and Ginsberg, *Arch. Biochem. Biophys.*, 150, 273–281 (1972). The structure of the isolated carbohydrate was determined by gas chromatography and mass spectrometry of the per-o-methylated derivatives prepared as described in Hakomori, *J. Biochem.*, 55, 205–208 (1964), and the results of the gas chromatography and mass spectrometry indicated that the isolated carbohydrate was the N3 isomer of formula I above. The presence of the Le$^a$ structure on the isolated N3 oligosaccharide was demonstrated by a hemagglutination inhibition assay performed as described in *Technical Manual of the American Association of Blood Banks*, pp. 392–393 (American Assoc. of Blood Banks, 8th ed., 1981). The presence of the Le$^x$ structure was also demonstrated as described below.

The isolated N3 was coupled to bovine serum albumin (BSA) by reductive amination using sodium cyanoborohydride according to the method described in Gray, *Complex Carbohydrates, Methods in Enzymology*, Vol. L pp. 155–160 (Ginsburg, ed., Academic Press, New York, 1978). Briefly, 6.8 mg (0.1 μmole) of bovine serum albumin (BSA, Sigma Chemical Co., St. Louis, Mo., product No. A7030), 10 mg (7.3 μmole) of purified N3 oligosaccharide, and 10 mg (0.159 mmole) of sodium cyanoborohydride (Sigma Chemical Co., St. Louis, Mo.) were dissolved in 2 ml of sterile 0.2M potassium phosphate buffer, pH 7.8, the reaction mixture filter sterilized through a 0.2 μm Gelman Sciences acrodisc filter (Baxter Scientific Products, McGaw Park, Ill.) into a sterile glass screw top culture tube. The reductive amination reaction was allowed to proceed by incubation at 37° C. for 6 weeks, after which the reaction mixture was diluted with 0.1M potassium phosphate buffer, pH 7.0 and passed over Bio-Gel P-2 (BioRad, Richmond, Calif.). The void volume containing the N3-BSA conjugate was exhaustively dialyzed against distilled water and subsequently lyophilized. The presence of the Le$^x$ antigen on N3-BSA was demonstrated by reaction in direct binding enzyme-linked fluorescence immunoassay (ELFA), performed as described below in Part B, except using monoclonal antibody to Le$^x$ (monoclonal antibody PM81, purchased from Hybritech Inc., San Diego, Calif., catalog number 0192) in place of the body fluid, and using biotinyl horse anti-mouse IgG (heavy and light chains) (Vector Laboratories) as the secondary labeled antibody.

B. Direct Binding Enzyme Linked Fluorescence Assay

To assay for antibodies to N3 in human serum, a fixed volume (100 μl) of N3-BSA was added to the wells of Microfluor "B" black polystyrene microtiter plates (purchased from Dynatech Laboratories, Alexandria, Va., USA) and incubated for 3 hrs at 37° C. and then overnight at 4° C. in a humidified chamber to coat the wells. N3-BSA was added at a concentration of 1.0 μg protein per ml in 0.1M NaHCO$_3$, pH 9.8. Unbound N3-BSA was removed by aspiration, and the remaining polystyrene protein binding sites were blocked by filling the wells with phosphate buffered saline (0.01M sodium phosphate buffer containing 0.15M NaCl, pH 7.3) containing 1% BSA (Sigma Chemical Co., St. Louis, Mo., product No. A7030) and incubating for 2 hours at 37° C. After aspirating the wells, 100 μl of sera, previously serially diluted in PBSA [0.01M sodium phosphate buffer containing 0.15M NaCl, 1% BSA (Sigma Chemical Co., St. Louis, Mo., product No. A4503), 0.1% Tween 20, and 0.02% NAN$_3$, pH 7.3] were added to wells and incubated overnight at 4° C. in a humidified chamber.

The sera tested were 15 normal human sera and 31 sera from human patients having gastrointestinal (GI) cancer collected on the day the patients had cancer surgery. Of the cancer sera, 15 were from patients with Stage B cancer, 12 from patients with Stage C cancer, and 4 from patients with Stage D cancer. Cancer stages were determined as described in Dukes, *J. Pathol. Bacteriol.*, 50, 527 (1940).

Next, the microtiter wells were washed 5 times with PBSA by repeatedly filling the wells and then aspirating the added liquid. Biotin-labeled goat anti-human IgG (heavy and light chain) (Vector Laboratories, Burlingame, Calif.) diluted 1:2000 in PBSA was added to the wells (100 μl per well) and allowed to incubate for 2 hours at 37° C. Following five PBSA washes done as described above, 100 μl of streptavidin-β-galactosidase (Bethesda Research Laboratories, Gaithersburg, Md.) diluted 1:2000 in PBSA, were added to each well, and the plates were incubated 1.5 hours at 37° C.

After a final five washes with PBSA done as described above, 100 μl of 0.1 mg/ml 4-methylumbelliferyl-β-D-galactopyranoside substrate in PBS, pH 7.5, were added to each well. After incubation for about 45–60 minutes, methylumbelliferone fluorescence was measured on a Microfluor Reader (Dynatech Laboratories) as relative fluorescence units (RFU) using an excitation wavelength of 365 nm and an emission wavelength of 450 nm. Readings were collected on floppy diskettes so that data reduction and curve fitting could be performed by computer.

Control wells were treated in an identical manner as described above, except for the following differences: control wells that lacked only N3-BSA ("without antigen controls"); control wells that lacked only cancer or normal sera ("without primary antibody controls"); control wells that received only a blocking step and with substrate alone ("substrate blank"). The without antigen controls and without primary antibody controls served to correct readings for non-specific binding of antibody and labeling reagents, while the substrate blank corrected for non-enzymatic substrate hydrolysis.

C. Calculation of Antibody Titers and Statistical Comparisons of Titers Obtained Titration data previously saved on diskettes were imported first into a spreadsheet (Lotus 1-2-3, Lotus Development Corporation, Cambridge, Mass., USA) which allowed duplicate measurements to be averaged and corrected for background. Background consisted of the means of corresponding duplicate without antigen controls.

Once corrected for background, the data were imported into the Titercalc program (Hewlett Packard, Santa Clara, Calif., USA), and non-linear regression was performed to a four-parameter logistic model using a Marquart-Levenburg non-linear regression algorithm. Representative output from this program is shown in FIG. 1.

Midpoint values of the resulting sigmoidal titration curves were used as a measure of the amount of antibody reactive with N3-BSA (i.e., antibody titer). The midpoint values obtained for GI cancer sera and normal sera were compared statistically using Fisher's "t" test of significance, and p values were obtained for the appropriate number of degrees of freedom.

Figure 2:
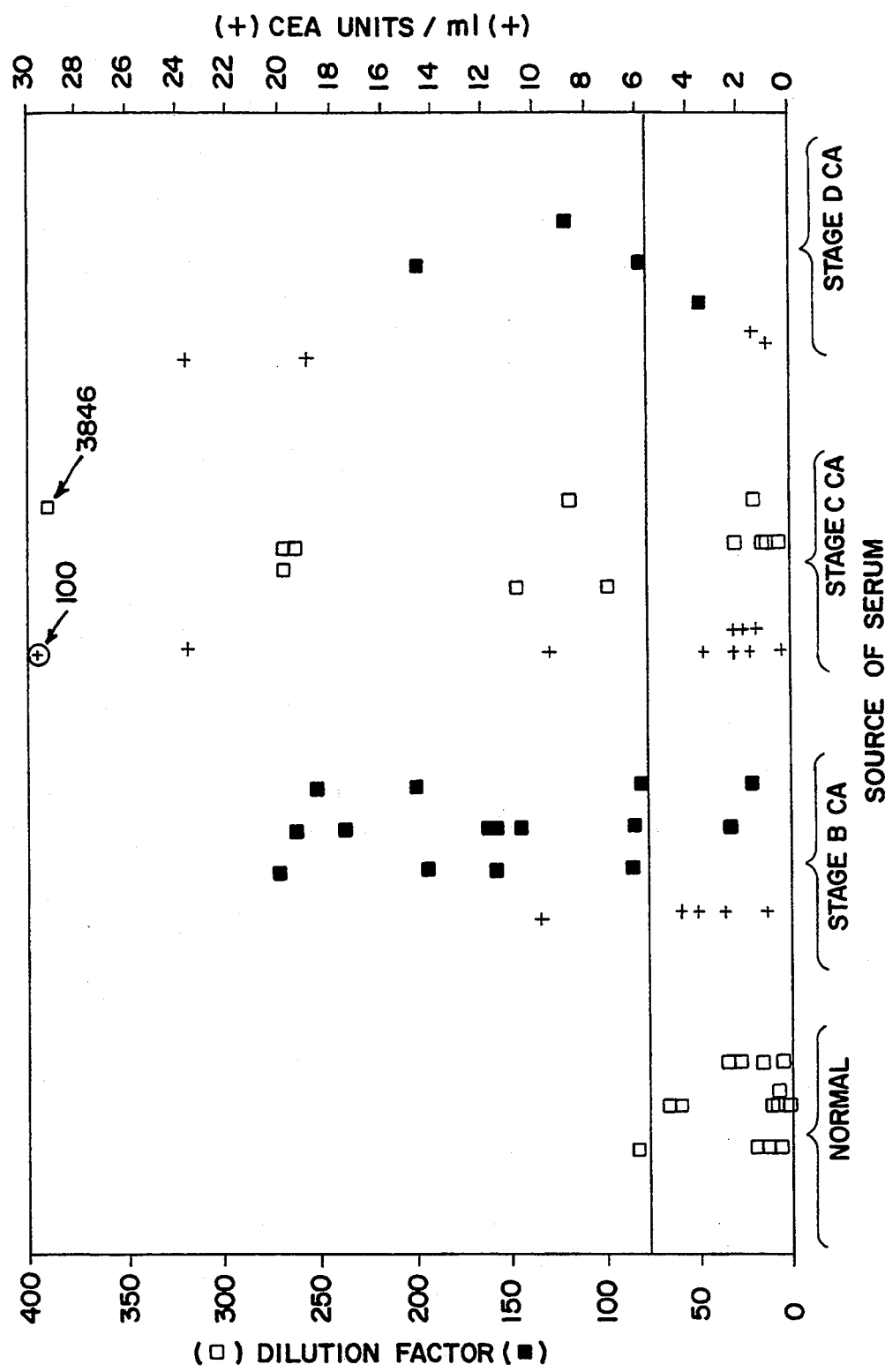
FIG. 2: Graph of gastrointestinal cancer stage versus titers of anti-N3 antibodies and versus units of carcinoembryonic antigen (CEA).

Midpoint values for normal sera and Stage B, Stage C and Stage D cancer sera were plotted as a scatter graph which is shown in FIG. 2. Corresponding "t" test calculations are shown in Table 1 below.

TABLE 1

STATISTICS ON GI CANCER SERA REACTIVITIES TO N3-BSA

|  | TOTAL CANCER | STAGE B CANCER | STAGE C CANCER | STAGE D CANCER | TOTAL NORMAL |
|---|---|---|---|---|---|
| NUMBER EXAMINED | 31 | 15 | 12 | 4 | 15 |
| AVERAGE R 2 |  |  | -.9195- |  |  |
| AVG. MID PT. (TITER) | — | 155 | 425 | 110 | 24 |
| T VALUE | — | 4.96 | 1.44 | 4.33 |  |
| p VALUE | — | p < 0.001 | 0.10 < p < 0.20 | p < 0.01 |  |

As shown in Table 1 and FIG. 2, antibody titers to N3 were higher for the GI cancer sera than for the normal sera. Also, levels of antibody to N3 were highest in earlier cancer stages.

Using a cut-off titer of 1:80, FIG. 2 shows that 14 out of 15 (93%) normal sera fell below this titer, while 13 of 15 (87%) Stage B, 7 of 12 (58%) Stage C and 3 of 4 (75%) Stage D carcinoma sera had titers above this dilution. The difference between the antibody levels of normal sera and Stage B or D cancer sera are highly significant (see Table 1). One of the Stage C sera had a very high titer (3846) which resulted in a high mean and large standard deviation for the Stage C data. If this one titer is deleted from the calculations, the mean titer for Stage C would be 114 (similar to the means for the Stage B and D sera). Also, this Stage C mean titer of 114 would be significantly different from the mean titer of the normal sera (p<0.01).

The data of FIG. 2 were also evaluated by chi square analysis of titers above and below cut-off titers of 1:100, 1:80 and 1:50. In all cases of cut-off titers used, the chi square analysis yielded highly significant differences (p<0.005) between normal sera and Stage B, Stage C or Stage D sera.

Levels of CEA antigen were also measured for some of the cancer patients using the Tandem E test for CEA (Hybritech, San Diego, Calif.) according to the manufacturer's directions. The results of this test are also shown in FIG. 2. Using a cut-off value of 3 CEA units/ml, 3 of 5 (60%) Stage B, 4 of 10 (40%) Stage C and 2 of 4 (50%) Stage D cancer sera contained elevated levels of CEA.

As shown in FIG. 2 and Table 2, the number of patients who exhibited elevated levels of CEA antigen was much lower than the number of patients who exhibited elevated levels of antibodies to N3 at all stages of cancer. Thus, by measuring antibody to N3 rather than levels of CEA antigen, a much greater number of patients having cancer are detected (see Table 2). In particular, the detection of a greater number of patients having Stage B cancer shows that the measurement of antibody to N3 detects cancer earlier than the measurement of CEA antigen in a substantial number of patients.

TABLE 2

| Cancer Stage | Percent of Patients Having Anti-N3 Titer over 1:80 | Percent of Patients Having Greater Than 3 CEA Units/ml |
|---|---|---|
| B | 87% | 60% |
| C | 58% | 40% |
| D | 75% | 50% |

I claim:

1. A method of screening for gastrointestinal cancer in a mammal comprising:
   (a) contacting a body fluid taken from the mammal with an octasaccharide having the following formula:

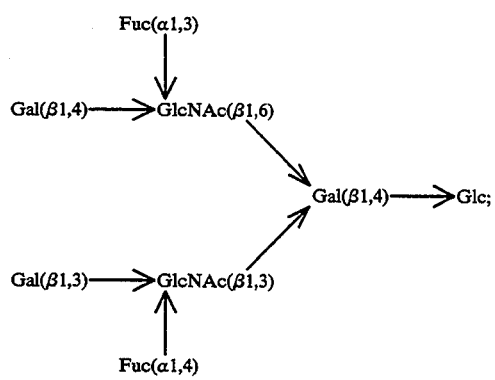

(b) measuring the amount of antibody from the body fluid bound to the octasaccharide; and
   (c) determining whether the amount of antibody measured in step (b) is higher than the amount of antibody to the octasaccharide normally present in the same type of body fluid taken from mammals of the same species that do not have cancer, an amount of antibody bound to the octasaccharide higher than is normally present in that body fluid being indicative of cancer.

2. The method of claim 1 wherein the body fluid is serum or plasma.

3. The method of claim 1 wherein the mammal is a human.

4. The method of claim 1 wherein the cancer present in the mammal is in an early stage of development.

5. The method of claim 1 wherein the octasaccharide is conjugated to a protein or polypeptide.

6. The method of claim 5 wherein the octasaccharide conjugate is immobilized on a solid surface.

7. The method of claim 5 wherein the octasaccharide conjugate is octasaccharide-bovine serum albumin.

8. The method of claim 7 wherein the octasaccharide-bovine serum albumin is immobilized on a solid surface.

9. The method of claim 1 wherein the amount of antibody is measured using a direct binding enzyme-linked fluorescence assay.

10. The method of claim 9 wherein the body fluid is human serum and the octasaccharide is conjugated to bovine serum albumin.

11. The method of claim 10 wherein the cancer present in the human is in an early stage of development.

12. A kit for detecting cancer in a mammal comprising a container of an octasaccharide having the following formula:

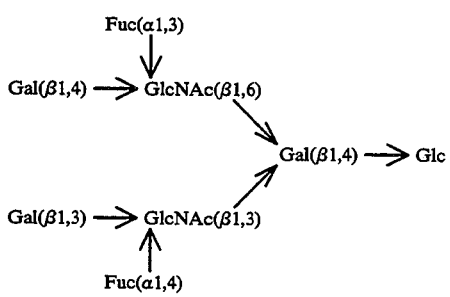

which has been conjugated to a protein or polypeptide.

13. The kit of claim 12 wherein the octasaccharide-conjugate is labeled.

14. A kit for detecting cancer in a mammal comprising a container of an octasaccharide having the following formula:

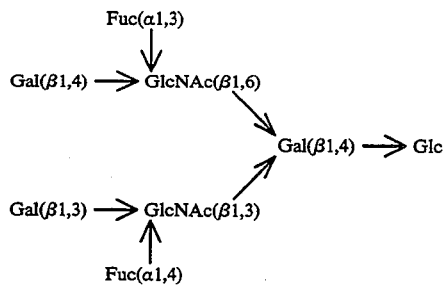

and a container of a secondary antibody or other reagent which binds to anti-octasaccharide antibodies.

15. The kit of claim 14 wherein the secondary antibody or other reagent is labeled.

16. The kit of claim 15 which comprises a container of a labeled secondary antibody, the secondary antibody being specific for human immunoglobulin.

17. The kit of claim 15 which comprises a container of a labeled secondary antibody, the label on the secondary antibody being biotin.

18. The kit of claim 14 wherein the octasaccharide is labeled.

19. The kit of claim 14 wherein the octasaccharide is conjugated to a protein or polypeptide.

20. The kit of claim 19 wherein the octasaccharide-conjugate is labeled.

* * * * *

UNITED STATES PATENT AND TRADEMARK OFFICE
CERTIFICATE OF CORRECTION

PATENT NO. : 5,376,531

DATED : December 27, 1994

INVENTOR(S) : Byron E. Anderson et al.

Page 1 of 3

It is certified that error appears in the above-indentified patent and that said Letters Patent is hereby corrected as shown below:

ON THE TITLE PAGE

Under the heading "OTHER PUBLICATIONS," Col. 2, line 14, please delete "238-245" and substitute --239-245--.

Page 2, Col. 2, line 8, before "sialyated" insert -- and --.

Page 2, Col. 2, line 33, delete "262≥271" and substitute --262-271 --.

Page 3, add the following missing publications:

--Singhal et al., "Profiles of Lewis$^x$-containing glycoproteins and glycolipids in sera of patients with adenocarcinoma," Cancer Res., 50, 1375-1380 (1990).

Smith et al., "Fractionation of sialyl oligosaccharides of human milk by ion-exchange chromatography," Anal. Biochem., 85, 602-608 (1978).

Springer et al., "Human carcinoma-associated precursor antigens of the blood group MN system and the host's immune responses to them," Prog. Allergy, 26, 42-96 (1979).

Springer, "T and Tn, general carcinoma autoantigens," Science, 224, 1198-1206 (1984).

UNITED STATES PATENT AND TRADEMARK OFFICE
CERTIFICATE OF CORRECTION

PATENT NO. : 5,376,531
DATED : December 27, 1994
INVENTOR(S) : Byron E. Anderson et al.

Page 2 of 3

It is certified that error appears in the above-indentified patent and that said Letters Patent is hereby corrected as shown below:

Springer et al., "Patient's immune response to CA-associated T antigen," in Cellular Oncology: New Approaches in Biology, Diagnosis and Treatment, pages 99-130 (Moloy and Nicolson eds., 1982).

Staab et al., "Are circulating CEA immune complexes a prognostic marker in patients with carcinoma of the gastrointestinal tract?," Br. J. Cancer, 42, 26 (1980).

Tal et al., "The agglutination of tumour cells *in vitro* by sera from tumour patients and pregnant women," Br. J. Cancer, 18, 111-119 (1964).

Thatcher et al., "Anti-T antibody in malignant melanoma patients," Cancer, 46, 1378 (1980).

Ura et al., "Studies on circulating antibody against carcinoembryonic antigen (CEA) and CEA-like antigen in cancer patients," Cancer Letters, 25, 283 (1985).

Yuan, et al., "Distribution of blood group antigens A, B, H, Lewis$^a$ and Lewis$^b$ in human normal, fetal, and malignant colonic tissue," Cancer Res., 45, 4499-4511 (1985).--

Col. 1, line 27, please delete ";".

UNITED STATES PATENT AND TRADEMARK OFFICE
CERTIFICATE OF CORRECTION

PATENT NO. : 5,376,531
DATED : December 27, 1994
INVENTOR(S) : Byron E. Anderson et al.

It is certified that error appears in the above-indentified patent and that said Letters Patent is hereby corrected as shown below:

Col. 13, line 9 in Table 1, delete "R 2" and substitute --$R^2$--.

IN THE CLAIMS

Col. 14, line 24, delete "I claim:" and substitute --We claim:--.

Claim 12, line 1, delete "detecting" and substitute --screening for--.

Claim 14, line 1, delete "detecting" and substitute --screening for--.

Signed and Sealed this

Seventeenth Day of September, 1996

Attest:

BRUCE LEHMAN

Attesting Officer

Commissioner of Patents and Trademarks